United States Patent
Beard et al.

(10) Patent No.: US 8,507,560 B2
(45) Date of Patent: Aug. 13, 2013

(54) PHARMACEUTICAL COMPOSITIONS COMPRISING 3,4-DIHYDROISOQUINOLIN-2(1H)-YL-3-PHENYLUREA DERIVATIVES HAVING FORMYL PEPTIDE RECEPTOR LIKE-1 (FPRL-1) AGONIST OR ANTAGONIST ACTIVITY

(75) Inventors: Richard L. Beard, Newport Beach, CA (US); John E. Donello, Dana Point, CA (US); Michael E. Garst, Newport Beach, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 65 days.

(21) Appl. No.: 13/300,729

(22) Filed: Nov. 21, 2011

(65) Prior Publication Data
US 2012/0142726 A1    Jun. 7, 2012

Related U.S. Application Data

(60) Provisional application No. 61/419,381, filed on Dec. 3, 2010.

(51) Int. Cl.
| | |
|---|---|
| *A01N 47/28* | (2006.01) |
| *A61K 31/17* | (2006.01) |
| *A61K 31/47* | (2006.01) |
| *A01N 43/42* | (2006.01) |
| *C07D 217/02* | (2006.01) |
| *C07C 273/00* | (2006.01) |
| *C07C 275/00* | (2006.01) |

(52) U.S. Cl.
USPC ............. 514/596; 514/309; 546/141; 564/47; 564/49; 564/53

(58) Field of Classification Search
USPC .................. 514/596, 309; 546/141; 564/47, 564/49, 53
See application file for complete search history.

(56) References Cited

U.S. PATENT DOCUMENTS

| | | | |
|---|---|---|---|
| 4,166,452 | A | 9/1979 | Generales |
| 4,256,108 | A | 3/1981 | Theeuwes |
| 4,265,874 | A | 5/1981 | Bonsen |
| 6,638,950 | B2 | 10/2003 | Duncia |

FOREIGN PATENT DOCUMENTS

| | | |
|---|---|---|
| WO | 03-082314 | 10/2003 |
| WO | 2005-047899 | 5/2005 |
| WO | 2005-056528 | 6/2005 |

OTHER PUBLICATIONS

Mar. 24, 2010, RN-1214189-38-4, Chemical Abstracts Service, Columbus, Ohio.
Apr. 13, 2001, RN-331238-30-3, Chemical Abstracts Service, Columbus, Ohio.
Apr. 13, 2001, RN-331252-08-5, Chemical Abstracts Service, Columbus, Ohio.
May 8, 2001, RN-334923-53-4, Chemical Abstracts Service, Columbus, Ohio.
Aug. 11, 2008, RN-1040195-78-5, Chemical Abstracts Service, Columbus, Ohio.
1980, Remington's Pharmaceutical Sciences, 16th Edition, Mack Publishing Company, Easton, Pa.
Abdul Rasheed et al, 2008, Concise and Efficient Synthesis of Highly Potent and Selective Dipeptidyl Peptidase II Inhibitors, Synthetic Communications, 38, 162-169.
Charles Serhan et al, 2011, Resolvins and Protectins in Inflammation Resolution, American Chemical Society, 111,5922-5943.
Driss El Kebir et al, Sep. 1, 2008, Opposing Regulation of Neutrophil Apoptosis Through the Formyl Peptide Receptor-Like 1/Lipoxin A4 Receptor: Implications for Resolution of Inflammation, Journal of Leukocyte Biology, 84 (3), 600-606.
Heinrich Stahl, 2002, Handbook of Pharmaceutical Salts, 329-345, Verlag Helvetica Chemica Acta—Zürich.
Mauro Perretti et al, 2010, Therapeutic Anti-Inflammatory Potential of Formyl-Peptide Receptor Agonists, Pharmacology & Research, 127, 175-188.
Youhong Cui et al, Oct. 1, 2002, Potential Role of the Formyl Peptide Receptor-Like 1 (FPRL1) in Inflammatory Aspects of Alzheimer's Disease, Journal of Leukocyte Biology, 72 (4), 628-635.
Patent Cooperation Treaty, Notification of Transmittal of the International Search Report and the Written Opinion of the International Searching Authority, or the Declaration, Form PCT/ISA/220, Int. App. No. PCT/US2011/061348, Mar. 16, 2012.

*Primary Examiner* — Kendra D Carter
(74) *Attorney, Agent, or Firm* — Doina G. Ene

(57) ABSTRACT

The present invention relates to a method of treating a disorder associated with modulation of the FPRL-1 receptor which comprises administering a therapeutically effective amount of a pharmaceutical composition comprising a 3,4-dihydroisoquinolin-2(1H)-yl-3-phenylurea derivative.

7 Claims, No Drawings

PHARMACEUTICAL COMPOSITIONS COMPRISING 3,4-DIHYDROISOQUINOLIN-2(1H)-YL-3-PHENYLUREA DERIVATIVES HAVING FORMYL PEPTIDE RECEPTOR LIKE-1 (FPRL-1) AGONIST OR ANTAGONIST ACTIVITY

RELATED APPLICATION

This application claims the benefit of U.S. Provisional Application Ser. No. 61/419,381, filed Dec. 3, 2010, the disclosure of which is hereby incorporated in its entirety herein by reference

FIELD OF THE INVENTION

The present invention relates generally to pharmaceutical compositions of certain 3,4-dihydroisoquinolin-2(1H)-yl-3-phenylurea derivatives and their use as modulators of the formyl peptide receptor. The invention relates specifically to the use of certain well-defined compounds having formyl peptide receptor like-1 (FPRL-1) agonist or antagonist activity.

BACKGROUND OF THE INVENTION

FPRL-1 (N-formyl peptide receptor like-1) is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide humanin, anti-inflammatory eicosanoid lipoxin A4 (LXA4) and glucocotricoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists.

Activation of FPRL-1 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner. In addition, FPRL1 has been shown to inhibit NK cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

It has now been discovered the use of a group of 3,4-dihydroisoquinolin-2(1H)-yl-3-phenylurea compounds as potent and selective FPRL-1 modulators. The present invention relates to a method of treating a disorder or a condition associated with modulation of the FPRL-1 receptor which comprises administering a therapeutically effective amount of a composition comprising a 3,4-dihydroisoquinolin-2(1H)-yl-3-phenylurea derivatives. The compounds in accordance with the present invention are thus of use in medicine, for example in the treatment of humans with diseases and conditions that are alleviated by FPRL-1 modulation. The term "modulator" as used herein, includes but is not limited to: receptor agonist, antagonist, inverse agonist, inverse antagonist, partial agonist, partial antagonist.

In one aspect, the invention provides a pharmaceutically composition comprising a therapeutically effective amount of a 3,4-dihydroisoquinolin-2(1H)-yl-3-phenylurea derivative selected from the group of compounds from Table 1:

| Number | Structure |
|---|---|
| Compound 1 | 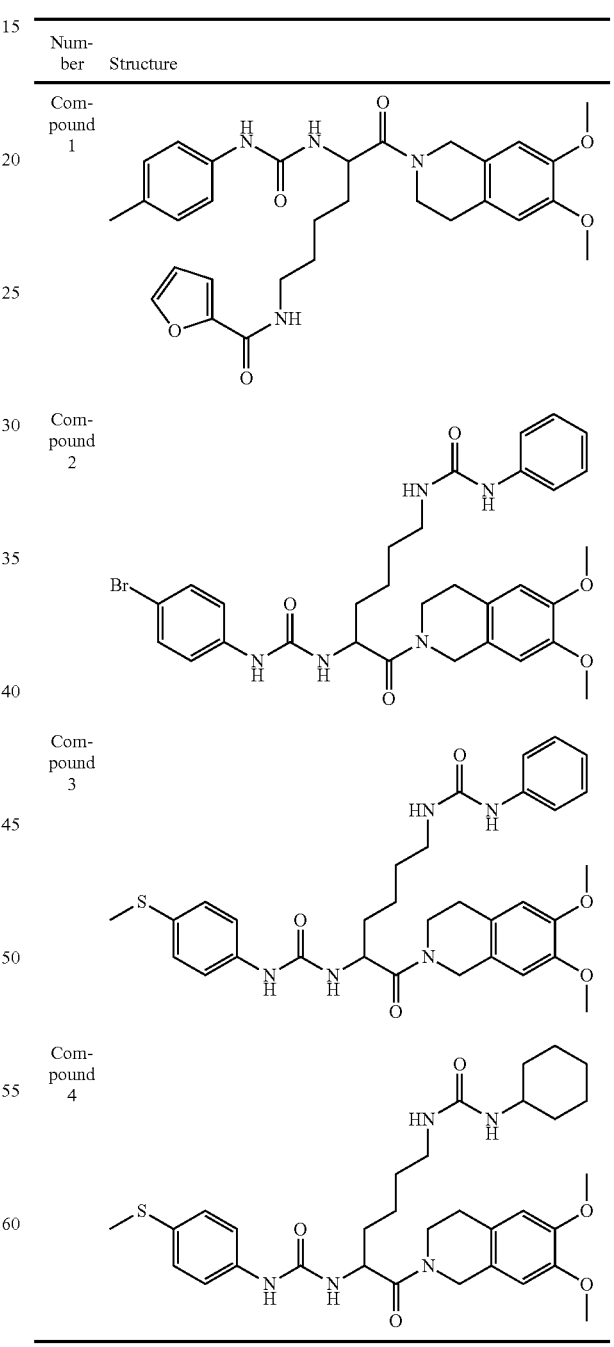 |
| Compound 2 | 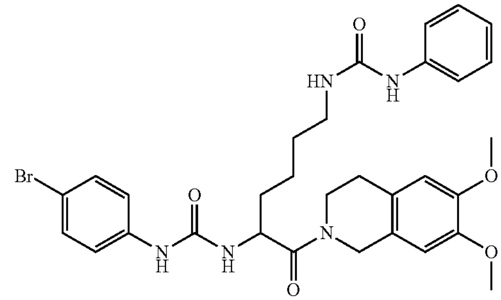 [SMILES: COc1cc2c(cc1OC)CN(C(=O)C(CCCCNC(=O)Nc1ccccc1)NC(=O)Nc1ccc(Br)cc1)CC2] |
| Compound 3 | 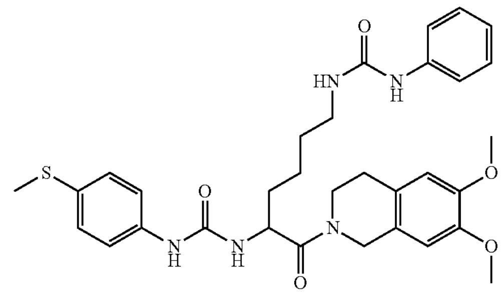 [SMILES: COc1cc2c(cc1OC)CN(C(=O)C(CCCCNC(=O)Nc1ccccc1)NC(=O)Nc1ccc(SC)cc1)CC2] |
| Compound 4 | 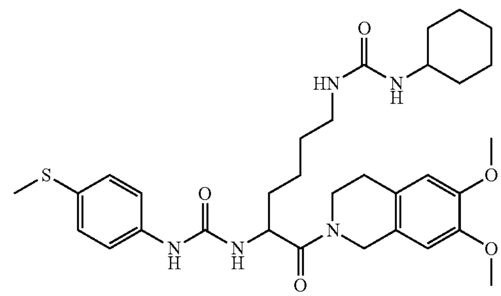 [SMILES: COc1cc2c(cc1OC)CN(C(=O)C(CCCCNC(=O)NC1CCCCC1)NC(=O)Nc1ccc(SC)cc1)CC2] |

The compounds from Table 1 are available from commercial sources such as Aurora Fine Chemicals LLC.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of the compounds of the invention which occur in their free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal& Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal& Camille G. Wermuth (Eds), Verlag Helvetica Chemica Acta-Zürich, 2002, 329-345).

Compounds of the invention and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor.

Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, asthma, atherosclerosis, human colon cancer, periodontitis, angina pectoris, post-surgical corneal inflammation, blepharitis, MGD, dermal wound healing, burns, skin-related diseases, including, arsenic keratoses, inflammatory and non-inflammatory acne, ichthyoses and other keratinization and hyperproliferative disorders of the skin, eczema, Darriers disease, lichen planus, prevention and reversal of glucocorticoid damage (steroid atrophy), rosacea, atopic dermatitis, acne, telangiectasia, discreet erythemas, erythema multiforme minor, erythema multiforme major seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188 and Charles N. Serhan et al. in "Resolvins and Protectins in Inflammation Resolution" Chem. Rev. 2011, 111, 5922-5943).

These compounds are useful for the treatment of mammals, including humans, with a range of conditions and diseases that are alleviated by the N-formyl peptide receptor like-1 receptor modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a 3,4-dihydroisoquinolin-2(1H)-yl-3-phenylurea derivative of Table 1 or a pharmaceutically acceptable salt thereof, for the manufacture of a medicament for the treatment of Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, telangiectasia, discreet erythemas, erythema multiforme minor, erythema multiforme major seborrheic dermatitis, actinic keratoses, viral warts, photoaging, rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The pharmaceutical compositions of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Biological Data

Biological activity of compounds according to Table1 is set forth in Table 2 below. CHO-Ga16 cells stably expressing FPRL1 were cultured in (F12, 10% FBS, 1% PSA, 400 µg/ml geneticin and 50 µg/ml hygromycin) and HEK-Gqi5 cells stable expressing FPR1 were cultured in (DMEM high glucose, 10% FBS, 1% PSA, 400 µg/ml geneticin and 50 µg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as $EC_{50}$ (nM) and efficacy values.

TABLE 2

| Number | Structure | FPRL-1 Ga16-CHO $EC_{50}$ (eff) |
|---|---|---|
| Compound 1 | 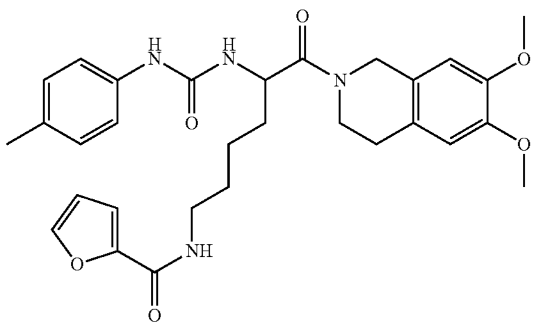 | 143 nM (0.61) |
| Compound 2 | 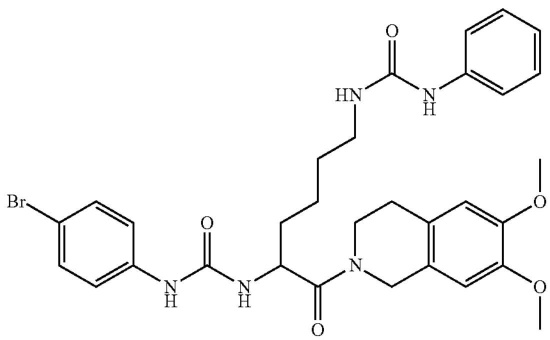 [SMILES: COc1cc2c(cc1OC)CN(C(=O)C(CCCCNC(=O)Nc1ccccc1)NC(=O)Nc1ccc(Br)cc1)CC2] | 91 nM (0.79) |
| Compound 3 | 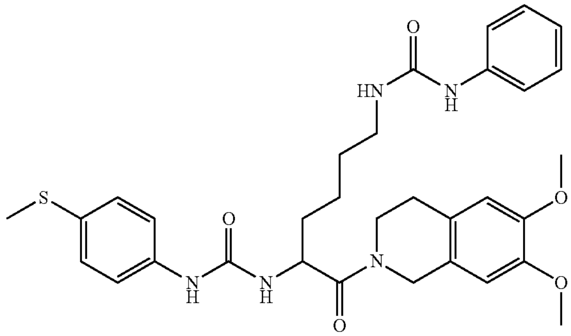 [SMILES: COc1cc2c(cc1OC)CN(C(=O)C(CCCCNC(=O)Nc1ccccc1)NC(=O)Nc1ccc(SC)cc1)CC2] | 32 nM (0.76) |
| Compound 4 | 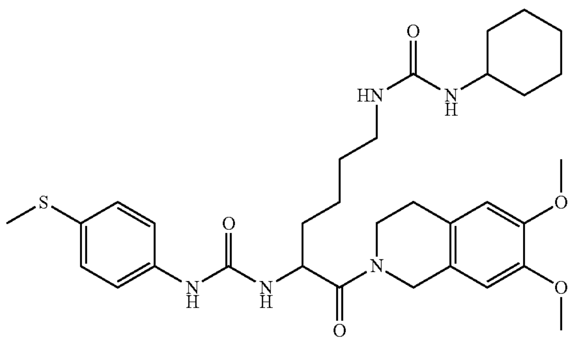 [SMILES: COc1cc2c(cc1OC)CN(C(=O)C(CCCCNC(=O)NC1CCCCC1)NC(=O)Nc1ccc(SC)cc1)CC2] | 59 nM (0.71) |

What is claimed is:

1. A method of modulating the N-formyl peptide receptor like-1 (FPRL-1) receptor comprising administering to a mammal in need thereof, a pharmaceutical composition comprising a therapeutically effective amount of at least one compound selected from:

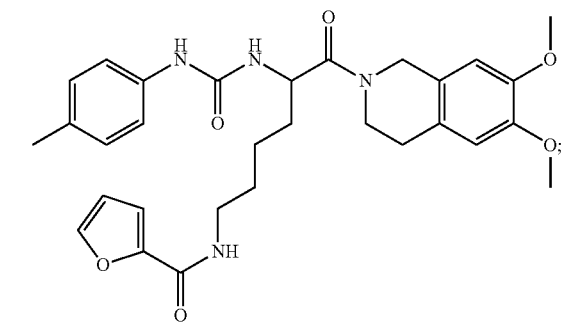

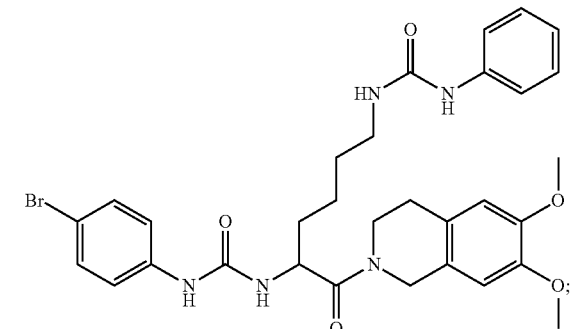

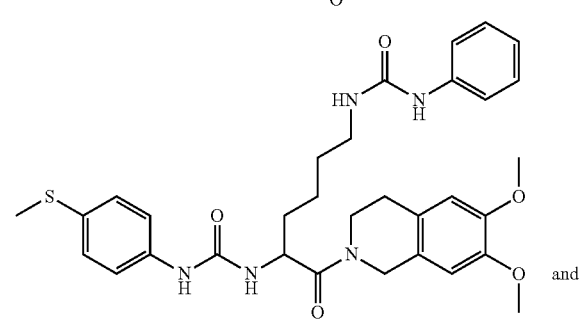

and

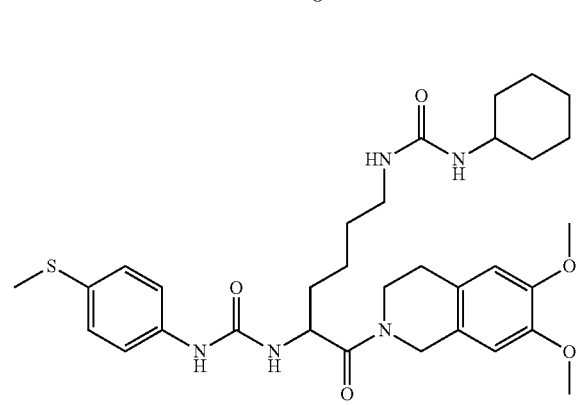

2. A pharmaceutical composition comprising as active ingredient a therapeutically effective amount of at least one compound according to claim 1 and a pharmaceutically acceptable adjuvant, diluent or carrier.

3. A pharmaceutical composition according to claim 2 wherein the compound is:

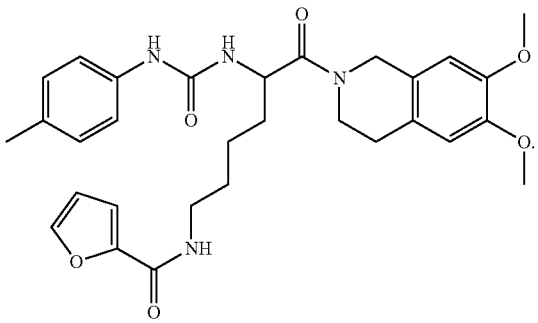

4. A pharmaceutical composition according to claim 2 wherein the compound is:

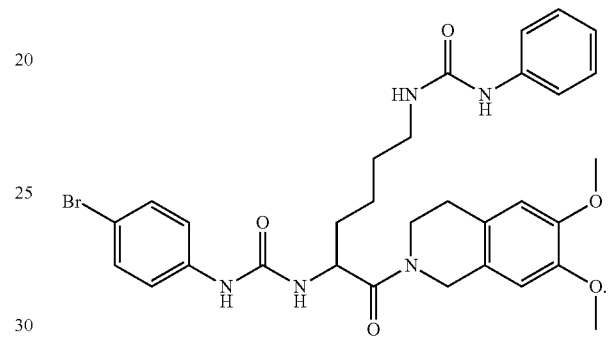

5. A pharmaceutical composition according to claim 2 wherein the compound is:

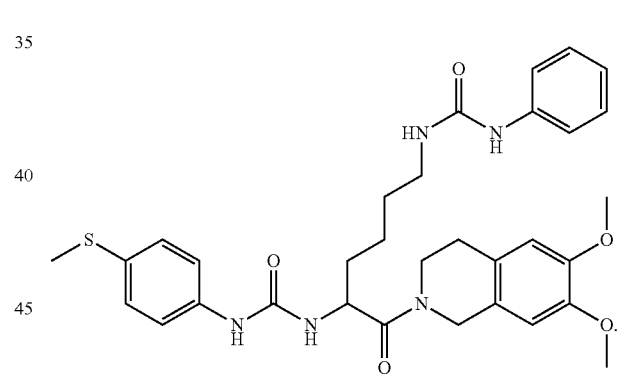

6. A pharmaceutical composition according to claim 2 wherein the compound is:

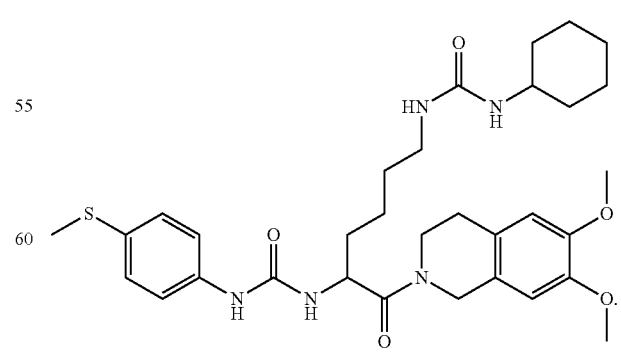

7. The method of claim 1 wherein the mammal is a human.

* * * * *

UNITED STATES PATENT AND TRADEMARK OFFICE
CERTIFICATE OF CORRECTION

| | | |
|---|---|---|
| PATENT NO. | : 8,507,560 B2 | Page 1 of 2 |
| APPLICATION NO. | : 13/300729 | |
| DATED | : August 13, 2013 | |
| INVENTOR(S) | : Richard L. Beard et al. | |

It is certified that error appears in the above-identified patent and that said Letters Patent is hereby corrected as shown below:

On the title page, in item (56), under "Other Publications", in column 2, line 23, delete "Chemica" and insert -- Chimica --, therefor.

On the title page, in item (56), under "Other Publications", in column 2, line 24, delete "Protential" and insert -- Potential --, therefor.

In the Specification

In column 1, line 14, after "reference" insert -- . --.

In column 1, line 36, delete "glucocotricoid-modulated" and insert -- glucocorticoid-modulated --, therefor.

In column 3, line 19, delete "Stahal&" and insert -- Stahl & --, therefor.

In column 3, line 20, delete "Chemica" and insert -- Chimica --, therefor.

In column 3, line 29, delete "Stahal&" and insert -- Stahl & --, therefor.

In column 3, line 30, delete "Chemica" and insert -- Chimica --, therefor.

In column 4, line 12, delete "vasuclar" and insert -- vascular --, therefor.

In column 4, line 17, delete "telangiectasis," and insert -- telangiectasia, --, therefor.

In column 4, line 39, delete "accosiated" and insert -- associated --, therefor.

In column 4, line 57, delete "pigement" and insert -- pigment --, therefor.

In column 5, line 4, delete "Darriers" and insert -- Darier's --, therefor.

In column 5, line 11, delete "degenartion," and insert -- degeneration, --, therefor.

In column 5, line 25, delete "degenartion," and insert -- degeneration, --, therefor.

In column 5, line 62, delete "vasuclar" and insert -- vascular --, therefor.

In column 5, line 67, delete "telangiectasis," and insert -- telangiectasia, --, therefor.

In column 6, line 22, delete "accosiated" and insert -- associated --, therefor.

Signed and Sealed this
Third Day of December, 2013

Margaret A. Focarino
*Commissioner for Patents of the United States Patent and Trademark Office*

CERTIFICATE OF CORRECTION (continued)
U.S. Pat. No. 8,507,560 B2

In column 6, line 39, delete "pigement" and insert -- pigment --, therefor.

In column 8, line 53, delete "Table1" and insert -- Table 1 --, therefor.